United States Patent [19]

Cox et al.

[11] Patent Number: 5,133,361
[45] Date of Patent: Jul. 28, 1992

[54] BIOPSY BRUSH

[76] Inventors: Lanita Cox, 25059 Wintergreen Ct., Newhall, Calif. 91381; Dennis Cox, 25479 Sheffield La., Saugus, Calif. 91350

[21] Appl. No.: 586,853

[22] Filed: Sep. 21, 1990

[51] Int. Cl.$^5$ .............................................. A61B 10/00
[52] U.S. Cl. ............................................................ 128/757
[58] Field of Search ................... 128/749, 756, 757, 759

[56] References Cited

U.S. PATENT DOCUMENTS

| | | | |
|---|---|---|---|
| 3,308,825 | 3/1967 | Cruse | 128/757 |
| 3,400,708 | 9/1968 | Scheidt | 128/757 |
| 4,027,658 | 6/1977 | Marshall | 128/757 |
| 4,562,847 | 1/1986 | Nydahl et al. | 128/757 |

Primary Examiner—Max Hindenburg
Attorney, Agent, or Firm—Donald D. Mon

[57] ABSTRACT

A biopsy brush for abrading and recovering samples of tissue to be investigated. A plurality of abrading elements are individually and separately spindled onto a flexible strand. The elements have an abrading periphery, and spacers which space these peripheries apart from one another. The flexibility of the strand where the elements are located enables the indivdual elements in the group of elements separately to deflect in response to changes in the shape of the tissue being abraded.

4 Claims, 1 Drawing Sheet

BIOPSY BRUSH

FIELD OF THE INVENTION

This invention relates to a biopsy brush which is drawn along a tissue surface to remove cells for investigation.

BACKGROUND OF THE INVENTION

It is known to draw a flexible cylindrical file-like or brush-like structure through or along a tissue surface. The objective is to cut or abrade the material, and to retain severed portion of it so they can be removed from the brush and studied. A principal disadvantage of conventional brushes is that they do exactly what their name implies. They scrape along the tissue, and hopefully some clings to the brush, but there is no means to assure retention of the separated material. Known brushes tend to be relatively rigid, with their elements close together. Basically they provide no place for the severed tissue to go.

It is an object of this invention to provide a biopsy brush whose abrading elements are spaced apart, are suitably flexible, and provide spaces between the elements to receive separated tissue.

BRIEF DESCRIPTION OF THE INVENTION

A biopsy brush according to this invention includes a linear flexible strand which can be drawn through or along a surface to be biopsied. A plurality of abrading elements is spindled as a stack on the strand. Each element is disc-like, and there is spacer means between adjacent elements.

Each element includes a periphery which is hard enough and suitably shaped as to abrade and remove tissue. Each element is sufficiently flexible so as to bend to conform to the surface being occupied and there is a spacing between these elements to receive the tissue.

The above and other features of this invention will be fully understood from the following detailed description and the accompanying drawings in which:

DETAILED DESCRIPTION OF THE INVENTION

Figure 1:
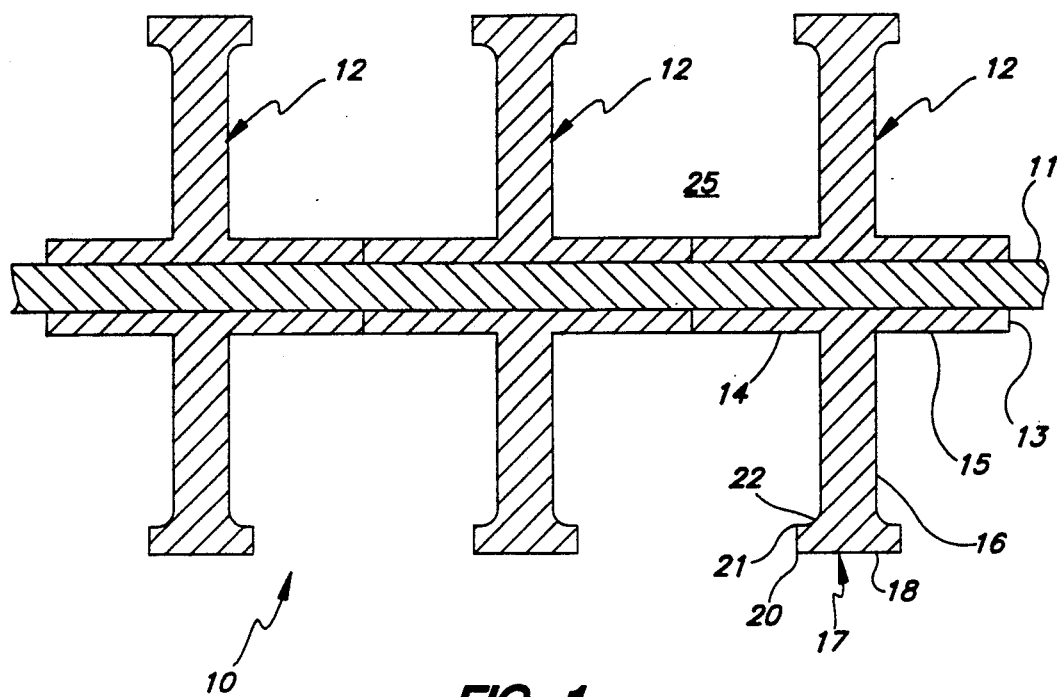
FIG. 1 is an axial cross-section of the presently preferred embodiment of the invention.
Figure 2:
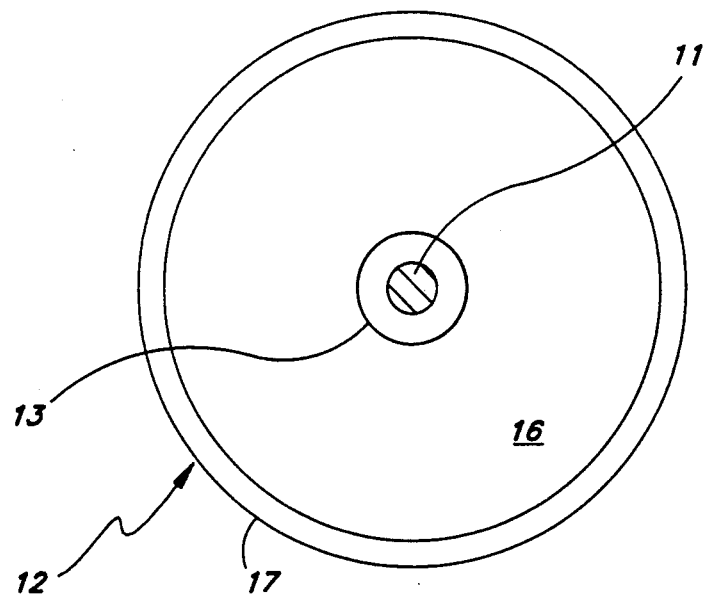
FIG. 2 is a side view of one of the abrading elements.

A biopsy brush 10 according to this invention is centered on a linear strand 11. The term "strand" is used to denote a thin flexible structure which may be made of any suitable material. Generally a sterilizable material such as a thin metal or plastic will be preferred, although twisted or woven materials could instead be used. Nylon line is the preferred material.

A plurality of abrasive elements 12 are strung on the strand. Because they are identical, only one will be described in detail. Conveniently each element will be formed integrally, preferably as a molded article. The presently preferred material for these elements is nylon.

Element 12 has a central spindle 13 with a pair of spacer segments 14, 15. The spindle has a central passage, and the strand is passed through it. Element 12 includes a web 16 which may be disc-like as shown, or if preferred may be formed as spokes for additional flexibility. However, a disc is more readily molded, and with a suitable thickness and selection of material it will be flexible enough.

An abrading rim 17 extends around the periphery of the web. It has a cylindrical outer wall 18, and two pairs of sharp edges, 20 at the outside, and 21, both at the vertex of a respective right angle. The web and edges 21 are joined by a 90 degree arc 22.

When the elements are spindled onto the strand, the spacer segments space the webs and abrading rims apart to form a space 25 to receive removed tissue. When the strand and the elements with it are drawn through or along tissue, the webs will deflect, and the edges will abrade the tissue. The geometry is such that the separated tissue will move into the spacing where it will remain when the brush is withdrawn.

The illustrated geometry resists "digging into" the tissue, but provides enough edge shapes to abrade the tissue. The term "abrade" includes both removal by surface rubbings and by sharp-edge excision.

Suitable dimensions for a molded nylon abrading element are as follows, the dimensions being in inches:

| | |
|---|---|
| Outer diameter of the sleeve: | 0.020 |
| Length of the sleeve: | 0.050 |
| Thickness of the web: | 0.010 |
| Radial dimension of the web from the outer diameter of the sleeve to arc 22: | 0.020 |
| Radius of arc 22: | 0.005 |
| Axial length of the rim: | 0.030 |
| Distance between edge 20 and 21: | 0.005 |

This invention is not to be limited by the embodiment shown in the drawings and described in the description, which is given by way of example and not of limitation, but only in accordance with the scope of the appended claims.

We claim:

1. A biopsy brush comprising: 'a linear extending flexible strand; and a plurality of abrading elements separately and adjacently spindled as a group on said strand, each said abrading element, comprising a sleeve adapted to pass said strand, a peripheral web around said sleeve, said web being stiffly flexible to bend while being drawn through or along tissue to be abraded, a rim extending peripherally around said web, having at least one edge suitably sharp to remove tissue cells, but without excessive penetration into the tissue, and spacer means spacing said rims and webs apart to from a spacing to receive a separated tissue, the flexibility of the strands where the elements are located enabling the elements in the group separately to deflect in response to change of shape of the tissue being abraded.

2. A biopsy brush according to claim 1 in which the spacer means comprises an extended segment of said sleeve.

3. A biopsy brush according to claim 1 in which said rim includes a substantially cylindrical outer surface, and two pairs of substantially right-angle edges, the axial dimensions of the web being shorter than the axial dimensions of the rim.

4. A biopsy brush according to claim 1 in which each abrading element is cast as a single molded article.

* * * * *